United States Patent [19]

Elion et al.

[11] 4,055,511
[45] Oct. 25, 1977

[54] CATALYST FOR PREPARATION OF 4-CYANOTHIAZOLE

[75] Inventors: Glenn R. Elion, Avenel; Arthur E. Klink, Lebanon, both of N.J.

[73] Assignee: Merck & Co., Inc., Rahway, N.J.

[21] Appl. No.: 666,713

[22] Filed: Mar. 15, 1976

[51] Int. Cl.$^2$ .................... B01J 23/88; B01J 27/10
[52] U.S. Cl. ........................... 252/435; 252/437; 252/439; 252/440; 252/441; 252/470
[58] Field of Search ............. 252/435, 439, 440, 470, 252/437, 441; 260/302 R

[56] References Cited

U.S. PATENT DOCUMENTS 3,240,806  3/1966  Bethell et al. ............... 252/439 X

FOREIGN PATENT DOCUMENTS 988,956  4/1965  United Kingdom ........... 260/302 R

*Primary Examiner*—W. J. Shine
*Attorney, Agent, or Firm*—David L. Rose; Richard A. Thompson; Harry E. Westlake

[57] ABSTRACT

4-Cyanothiazole is prepared by the catalytic vapor phase ammoxidation of Δ3-4-methylthiazoline or 4-methylthiazole, using as catalyst a novel composition comprising a slurried chromium cobalt molybdate. The process affords high selectivity in the production of 4-cyanothiazole.

3 Claims, No Drawings

CATALYST FOR PREPARATION OF 4-CYANOTHIAZOLE

This invention relates to novel chemical compositions and to a process for the production of 4-cyanothiazole from Δ3-4-methylthiazoline or 4-methylthiazole using such compositions as catalysts.

One of the problems inherent in an ammoxidation system for making cyanothiazole from 4-methylthiazole or Δ3-4-methylthiazoline and particularly in a system employing excess oxygen in the reactant stream is undesirable combustion of organic reactant and ammonia to unwanted by-products. This, of course, adds to process costs in that more reactant is required to produce a given amount of cyanothiazole (e.g., yields are reduced) and also larger capital investment is required to build a plant for a given capacity. Thus, a reduction in the undesired combustion of ammonia and organic reactant with the attendant yield increase is a desirable objective.

It has now been found that in the catalytic vapor phase ammoxidation of Δ3-4-methylthiazoline or 4-methylthiazole to 4-cyanothiazole, the yield of 4-cyanothiazole can be significantly increased and ammonia and hydrocarbon decomposition mitigated by employing the novel catalyst described herein. An advantage of the present invention is that the catalyst is more selective for production of the desired 4-cyanothiazole. Another advantage is that an adiabatic or isothermal-type reactor can be utilized which results in allowance of temperature fluctuations without any significant decrease in the high selectivity for 4-cyanothiazole. Also, when Δ3-4-methylthiazoline is used in the reactant stream, 4-methylthiazole is produced first, and when all of the 4-methylthiazole is not converted to 4-cyanothiazole, it is not decomposed by the catalyst of this invention to undesirable by-products.

Thus according to the invention, there is provided a process for the preparation of 4-cyanothiazole from 4-methylthiazole or Δ3-4-methylthiazoline which comprises passing as a reactant stream, a gaseous mixture comprising:

1. 4-methylthiazole or Δ3-4-methylthiazoline;
2. ammonia;
3. oxygen; and
4. water as steam, and the improvement comprises passing said reactant stream over a slurried chromium cobalt molybdate ammoxidation catalyst at a temperature of 360° to 450° C.

Another aspect of this invention is that the catalyst contains one or more additives of the group potassium hydroxide (KOH), ferric chloride ($FeCl_3$), ammonium orthophosphate $(NH_4)_2HPO_4$, telluric acid ($H_2TeO_4$), potassium sulfate ($K_2SO_4$), or vanadyl sulfate ($VOSO_4$).

More preferably the mole ratios of said reactant stream are:

ammonia:4-methylthiazole or Δ3-4-methylthiazoline 1:1 to 2:1;
oxygen:4-methylthiazoline or Δ3-4-methylthizaoline 0.5:1 to 200:1;
water as steam:4-methylthiazole or Δ3-4-methylthiazoline 0.001:1 to 10:1;
and said catalyst has a molybdenum:cobalt molar ratio of from 1.20:1.00 to 1.05:1.00 a chromium chloride:cobalt molybdate molar ratio of from 0.6:1 to 1.4:1, and an additive:cobalt molybdate molar ratio of from 0.001:1 to 0.08:1.

The novel ammoxidation catalyst of this invention is a slurried chromium cobalt molybdate having a molybdenum:cobalt molar ratio of from 1.20:1.00 to 1.05:1.00, and a chromium chloride:cobalt molybdate molar ratio of from 0.6:1.0 to 1.4:1.0. Preferably the chromium chloride:cobalt molybdate molar ratio is from 0.8:1 to 1.1:1.

More preferred ranges for the additives to the cobalt molybdate are potassium hydroxide from 0.01:1 to 0.08:1; ferric chloride from 0.001:1 to 0.01:1; ammonium orthophosphate from 0.001:1 to 0.04:1; telluric acid from 0.01:1 to 0.05:1; potassium sulfate 0.01:1 to 0.08:1; and vanadyl sulfate from 0.01:1 to 0.08:1.

The novel catalyst is prepared by contacting solid cobalt molybdate having a particle size of less than 10μ with chromic chloride, preferably in aqueous solutions. This is in effect a slurrying of the cobalt molybdate with chromic chloride solution, and is so referred to in describing this invention. The slurry mixture is concentrated to a thick paste, dried and then fired, preferably for about 12 hours at about 450° C.

The reslurried catalyst can then be supported on one of the commercially available inert supports such as silica ($SiO_2$), alumina, pumice, calcium sulfate and magnesium oxide and other conventional supports. The preferred inert support is silica. By the term "inert" is meant that the support does not have any deleterious effects on the catalyst. The catalyst is supported by jetatomizing the catalyst to a powder and then mixing it with aqueous colloidal silica to obtain a catalyst with high physical strength. The catalyst can be up to 80% by weight of the total weight of catalyst plus support. A more desirable weight range of the catalyst is 55–65%.

In carrying out the process of the invention, the reactor and attendant equipment is prepared in the usual way, the reactor being charged with catalyst and otherwise prepared for start-up, including the heating up of the catalyst if desired. The 4-methylthiazole or Δ3-4-methylthiazoline, ammonia, oxygen and water (steam) are passed over the catalyst at reaction conditions and at certain mole percent ratios. For an isothermal reactor system, the temperature range can be from 360° C. to 430° C. A more desired range for an isothermal reactor system is 395° C. to 405° C. For an adiabatic reactor system, the outlet temperature range is from about 390° C. to 450° C. A more desirable temperature range for an adiabatic reactor system is 420° C. to 440° C.

The contact time for a reactant stream is the time that the reactants are in contact with the catalyst composition. For an isothermal or adiabatic reactor system, the contact time can be from about 0.1 to 1.0 seconds. A more desirable range is 0.25 to 0.35 seconds.

The following examples are given for the purpose of illustration and not for the purpose of limiting the scope of invention.

EXAMPLE 1

This example illustrates the preparation of the chromium cobalt molybdate slurry catalyst. The cobalt molybdate may be prepared by techniques known in the art. That is, cobalt molybdate is precipitated by reacting cobalt sulfate or nitrate with ammonium molybdate. However, the subsequent treatment and slurry techniques resulting in this highly active catalyst are unobvious and novel.

1. To 200 milliliters (ml.) of water is added 145.0 grams (gm.) of cobalt nitrate ($Co(NO_3)_2 \cdot 6H_2O$) and the mixture is heated to 40° C. with stirring until all the material is in solution.

2. To 250 ml. of water is added 90 gm. of ammonium paramolybdate $(NH_4)_4Mo_7O_{24}.4H_2O$ and the mixture heated to 40° C. with stirring until all the material is in solution.

Solutions obtained in Steps 1. and 2. above are mixed together and then 8N ammonium hydroxide $(NH_4OH)$ is added until the pH remains at 5.8 for one hour. A purple material precipitates from the solution.

The resulting precipitate is filtered and washed with 200 ml. of water to remove the excess cobalt nitrate and ammonia; then the filter cake is dried to about 5% water in a vacuum oven at 15-20 millimeters Hg at 80°-90° C.

The filter cake is fired for 16 to 24 hours in air at 450° C., and then the catalyst is jetatomized to a particle size of about 1-2μ. A phase change occurs during jetatomization forming a low density green powder. By jetatomizing is meant fluid energy milling using air or nitrogen to obtain particle sizes less than 10μ and typically in the 0.5μ to 5μ particle size range. The molar ratio of molybdenum:cobalt is 1.15:1.00.

SLURRY CHROMIUM COBALT MOLYBDATE CATALYST

To 20 ml. of water is added 40 gm. of chromium chloride $(CrCl_3.6H_2O)$ with heating to 50° C. while stirring until all the material is in solution; then add 40 gm. of the cobalt molybdate. It is at this stage of the catalyst preparation that the additive agents described above can be added to the catalyst. In this catalyst preparation, 0.8 gm. of potassium sulfate is added.

The reslurry mixture is made into a thick paste by evaporating the water, dried in a vacuum oven at 15-20 mm. Hg at 80°-95° C., and finally fired for 12 hours at 450° C. The finished catalyst is sized to 16-30 mesh (Handbook of Chemistry and Physics, 40th Edition, pg. 3357, U.S. Standard Sieve Series).

EXAMPLE 2

In this example, the catalyst prepared according to Example 1 is utilized.

Three and six-tenths (3.6) cubic centimeters (cc.) of catalyst are loaded into a 0.635 centimeter (cm.) inner diameter (ID) stainless steel isothermal reactor tube. Said isothermal reactor is connected to an on-line gas chromatograph to analyze the reactants and products.

The feed composition is adjusted to enter the reactor at the rate of 0.02 cc./minute of Δ3-4-methylthiazoline; air at 625 cc./minute; and concentrated ammonium hydroxide (28%) at 0.02 cc./minute. The reactor temperature is 415° C. At this temperature, Δ3-4-methylthiazoline is quantitatively converted to 4-methylthiazole in the attendant equipment before it comes into contact with the catalyst bed. Of the 4-methylthiazole that comes into contact with the catalyst, 50% is converted into products. Of the said 4-methylthiazole that is converted into products, 75% is converted to 4-cyanothiazole, 10% is converted to thiazole, and the remaining 15% is converted to by-products. Thus, the selectivity to 4-cyanothiazole is 75%.

EXAMPLE 3

The catalyst utilized in this example is similar to that prepared in Example 1 except that vanadyl sulfate (VOSO$_4$) and telluric acid (H$_2$TeO$_4$) instead of potassium sulfate are utilized as the additives. The reactor conditions are the same as those in Example 2.

Three and six tenths cc. of catalyst are loaded in the reactor tube. The feed composition is adjusted to enter the reactor at the rate of 0.02 cc./minute of 4-methylthiazole; air at 600 cc./minute and the concentrated ammonium hydroxide (28% at 0.02 cc./minute. The conversion and selectivity to 4-cyanothiazole is given in the Tables below.

Table I

Catalyst (molar ratios)
VOSO$_4$ 0.01/Cr 0.18/Co 1.00/Mo 1.15

| Reactor Temp. (° C.) | Conversion (%) | Selectivity (%) |
|---|---|---|
| 420 | 56 | 70 |
| 410 | 44 | 73 |
| 400 | 32 | 76 |
| 390 | 23 | 81 |
| 380 | 14 | 87 |

Table II

Catalyst (molar ratios)
Te 0.03/Cr 0.80/Co 1.00/Mo 1.15

| Reactor Temp. (° C.) | Conversion (%) | Selectivity (%) |
|---|---|---|
| 420 | 50 | 70 |
| 410 | 36 | 73 |
| 400 | 26 | 76 |
| 390 | 17 | 78 |
| 380 | 12 | 80 |

EXAMPLE 4

The catalyst utilized in this example is similar to that prepared in Example 1 except that ammonium orthophosphate and ferric chloride are added in addition to postassium sulfate. The molar ratios of the additives to the cobalt molybdate are phosphorous:cobalt, 0.006:1; iron:cobalt, 0.004:1; and potassium:cobalt 0.02:1.

The same reactor conditions and feed composition are employed in this example as utilized in Example 3. The conversion and selectivity to 4-cyanothiazole is given in Table III.

Table III

| Reactor Temp. (° C.) | Conversion (%) | Selectivity (%) |
|---|---|---|
| 420 | 73 | 68 |
| 410 | 56 | 70 |
| 400 | 41 | 74 |
| 390 | 29 | 77 |
| 380 | 21 | 80 |

EXAMPLE 5

This example illustrates the novel catalyst when the molar ratios of the components are chromium chloride 0.80:cobalt 1.00:molybdenum 1.10:potassium sulfate 0.075. Also, gaseous $NH_3$ is used rather than concentrated $NH_4OH$.

The feed composition contains 4-methylthiazole as the organic reactant. The feed enters the reactor at the rate of 0.02 cc./minute of 4-methylthiazole; air 600 cc./minute and 1.3 moles of $NH_3$ per mole of 4-methylthiazole. The conversion and selectivity to 4-cyanothiazole is given in Table IV.

Table IV

| Reactor Temp. (° C.) | Conversion (%) | Selectivity (%) |
|---|---|---|
| 420 | 68 | 69 |
| 410 | 55 | 71 |
| 400 | 42 | 73 |
| 390 | 31 | 75 |
| 380 | 22 | 77 |

EXAMPLE 6

This example illustrates the use of the cobalt molybdate catalyst. Note the percent selectivity compared to the slurried catalyst.

Into a 0.635 cm. stainless steel reactor tube is loaded 3.6 cc. of cobalt molybdate catalyst. The reactor is placed in an isothermal gas chromatographic reactor system. The feed composition is adjusted to enter the reactor at 0.018 cc./minute of 4-methylthiazole, 0.013 cc./minute of concentrated NH$_4$OH (28%) and 600 cc./minute of dry air. Under the temperature conditions as shown in Table V, the following conversion and selectivity to 4-cyanothiazole is given.

Table V

| Reactor Temp. (° C.) | Conversion (%) | Selectivity (%) |
|---|---|---|
| 420 | 69 | 43 |
| 410 | 54 | 54 |
| 400 | 43 | 57 |
| 390 | 34 | 60 |
| 380 | 23 | 64 |

What is claimed is:

1. A catalyst composition prepared by the process of adding to a solution of chromium chloride and cobalt molybdate a compound selected from the group consisting of potassium hydroxide, ferric chloride, ammonium orthophosphate, telluric acid, potassium sulfate and vanadyl sulfate wherein the molar ratio of molybdenum:cobalt is from 1.20:1.00 to 1.05:1.00; the molar ratio of the chromium chloride:cobalt molybdate is 0.6:1 to 1.4:1 and the molar ratio of a compound selected from said group to cobalt molybdate is 0.01:1 to 0.08:1 for potassium hydroxide; 0.001:1 to 0.01:1 for ferric chloride; 0.001:1 to 0.04:1 for ammonium orthophosphate; 0.01:1 to 0.05:1 for telluric acid; 0.01:1 to 0.08:1 for potassium sulfate; and 0.01:1 to 0.08:1 for vanadyl sulfate, and drying and firing for about 12 hours at 450° C.

2. A catalyst composition consisting essentially of chromium chloride:cobalt molybdate wherein the molar ratio of molybdenum:cobalt is from 1.20:1.00 to 1.05:1.00 and the molar ratio of chromium chloride:cobalt molybdate is from 0.6:1.0 to 1.4:1.0.

3. A catalyst composition according to claim 2 wherein the molar ratio of chromium chloride:cobalt molybdate is from 0.8:1.0 to 1.1:1.0.

* * * * *